(12) United States Patent
Bernate et al.

(10) Patent No.: US 10,787,683 B1
(45) Date of Patent: *Sep. 29, 2020

(54) ELECTROPORATION CUVETTES FOR AUTOMATION

(71) Applicant: Inscripta, Inc., Boulder, CO (US)

(72) Inventors: Jorge Bernate, Boulder, CO (US); Phil Belgrader, Boulder, CO (US); Don Masquelier, Boulder, CO (US); Vlorent Morina, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/927,937

(22) Filed: Jul. 13, 2020

Related U.S. Application Data

(63) Continuation of application No. 16/109,156, filed on Aug. 22, 2018, now Pat. No. 10,738,327.

(60) Provisional application No. 62/551,069, filed on Aug. 28, 2017.

(51) Int. Cl.
*C12N 15/87* (2006.01)
*C12M 1/42* (2006.01)
*C12M 1/12* (2006.01)

(52) U.S. Cl.
CPC .............. *C12N 15/87* (2013.01); *C12M 25/02* (2013.01); *C12M 35/02* (2013.01)

(58) Field of Classification Search
CPC ...... C12M 35/02; C12M 35/04; C12M 25/02; C12M 41/48; C12M 41/18; C12M 23/44; C12M 23/12; C12M 23/06; C12M 29/04; C12N 15/87; C12N 15/8207; C12N 15/8206; C12N 13/00; B01L 7/00; B01L 7/3527; B01L 2200/16; B01L 2200/028; B01L 2300/04; B01L 2300/12; B01N 33/48728; A61N 1/306; A61K 38/00
See application file for complete search history.

(56) References Cited

U.S. PATENT DOCUMENTS

| | | | |
|---|---|---|---|
| 5,710,381 | A | 1/1998 | Atwood et al. |
| 5,792,943 | A | 8/1998 | Craig |
| 6,074,605 | A | 6/2000 | Meserol et al. |
| 6,127,141 | A | 10/2000 | Kopf |
| 6,150,148 | A | 11/2000 | Nanda et al. |
| 6,482,619 | B1 | 11/2002 | Rubinsky et al. |

(Continued)

FOREIGN PATENT DOCUMENTS

| | | |
|---|---|---|
| EP | 2135626 | 1/2011 |
| EP | 1766004 | 8/2016 |

(Continued)

OTHER PUBLICATIONS

Bao, et al., "Genome-scale engineering of *Saccharomyces cerevisiae* with single-nucleotide precision", Nature Biotechnology, doi:10.1038/nbt.4132, pp. 1-6 (May 7, 2018).

(Continued)

*Primary Examiner* — Michael L Hobbs
(74) *Attorney, Agent, or Firm* — Sarah Brashears; Dianna L. DeVore

(57) ABSTRACT

The present disclosure relates to an electroporation device that may include many electroporation units and electroporation systems that can be used in an automated environment, e.g., as one station or module in a multi-station or multi-module cell processing environment.

18 Claims, 7 Drawing Sheets

(56) References Cited

U.S. PATENT DOCUMENTS

| | | |
|---|---|---|
| 6,654,636 B1 | 11/2003 | Dev et al. |
| 6,746,441 B1 | 6/2004 | Hofmann et al. |
| 6,837,995 B1 | 1/2005 | Vassarotti et al. |
| 7,029,916 B2 | 4/2006 | Dzekunov et al. |
| 7,141,425 B2 | 11/2006 | Dzekunov et al. |
| 7,166,443 B2 | 1/2007 | Walker et al. |
| 7,422,889 B2 | 9/2008 | Sauer et al. |
| 8,110,112 B2 | 2/2012 | Alburty et al. |
| 8,153,432 B2 | 4/2012 | Church et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang |
| 8,726,744 B2 | 5/2014 | Alburty et al. |
| 8,758,623 B1 | 6/2014 | Alburty et al. |
| 8,932,850 B2 | 1/2015 | Chang et al. |
| 9,029,109 B2 | 5/2015 | Hur et al. |
| 9,063,136 B2 | 6/2015 | Talebpour et al. |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,776,138 B2 | 10/2017 | Innings et al. |
| 9,790,490 B2 | 10/2017 | Zhang et al. |
| 9,896,696 B2 | 2/2018 | Begemann et al. |
| 9,982,279 B1 | 5/2018 | Gill et al. |
| 10,017,760 B2 | 7/2018 | Gill et al. |
| 10,738,327 B2 * | 8/2020 | Bernate et al. ........ C12N 15/87 |
| 2002/0139741 A1 | 10/2002 | Kopf |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0001865 A1 | 1/2006 | Bellalou et al. |
| 2006/0224192 A1 | 10/2006 | Dimmer et al. |
| 2007/0042427 A1 | 2/2007 | Gerdes et al. |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0002812 A1 | 1/2011 | Asogawa et al. |
| 2011/0003303 A1 | 1/2011 | Pagano et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2013/0005025 A1 | 1/2013 | Church et al. |
| 2013/0015119 A1 | 1/2013 | Pugh et al. |
| 2013/0196441 A1 | 8/2013 | Rubinsky et al. |
| 2014/0068797 A1 | 3/2014 | Doudna et al. |
| 2014/0121728 A1 | 5/2014 | Dhillon et al. |
| 2014/0199767 A1 | 7/2014 | Barrangou et al. |
| 2014/0273226 A1 | 9/2014 | Wu |
| 2014/0350456 A1 | 11/2014 | Caccia |
| 2015/0072413 A1 | 3/2015 | Zenhausern et al. |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0297887 A1 | 10/2015 | Dhillon et al. |
| 2016/0024529 A1 | 1/2016 | Carstens |
| 2016/0053272 A1 | 2/2016 | Wurtzel et al. |
| 2016/0053304 A1 | 2/2016 | Wurtzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0272961 A1 | 9/2016 | Lee |
| 2016/0281047 A1 | 9/2016 | Chen et al. |
| 2016/0289673 A1 | 10/2016 | Huang et al. |
| 2016/0298074 A1 | 10/2016 | Dai |
| 2016/0298134 A1 | 10/2016 | Chen et al. |
| 2016/0310943 A1 | 10/2016 | Woizenko et al. |
| 2016/0313306 A1 | 10/2016 | Ingber et al. |
| 2016/0367991 A1 | 12/2016 | Cepheid |
| 2017/0002339 A1 | 1/2017 | Barrangou et al. |
| 2017/0029805 A1 | 2/2017 | Li et al. |
| 2017/0051310 A1 | 2/2017 | Doudna et al. |
| 2017/0073705 A1 | 3/2017 | Chen et al. |
| 2017/0218355 A1 | 3/2017 | Buie et al. |
| 2017/0159045 A1 | 6/2017 | Serber et al. |
| 2017/0191123 A1 | 7/2017 | Kim et al. |
| 2017/0240922 A1 | 8/2017 | Gill et al. |
| 2017/0283761 A1 | 10/2017 | Corso |
| 2017/0307606 A1 | 10/2017 | Hallock |
| 2017/0349874 A1 | 12/2017 | Jaques et al. |
| 2018/0023045 A1 | 1/2018 | Hallock et al. |
| 2018/0051327 A1 | 2/2018 | Blainey et al. |
| 2018/0142196 A1 | 5/2018 | Coppeta et al. |
| 2018/0155665 A1 | 6/2018 | Zenhausern et al. |
| 2018/0169148 A1 | 6/2018 | Adair et al. |
| 2018/0179485 A1 | 6/2018 | Borenstein et al. |
| 2019/0136224 A1 | 5/2019 | Garcia Dominguez et al. |

FOREIGN PATENT DOCUMENTS

| | | |
|---|---|---|
| EP | 2459696 | 11/2017 |
| WO | WO 2003/057819 | 7/2001 |
| WO | WO 2009/091578 | 7/2009 |
| WO | WO 2011/143124 | 11/2011 |
| WO | WO 2013/142578 | 9/2013 |
| WO | WO 2013/176772 | 11/2013 |
| WO | WO 2014/018423 | 1/2014 |
| WO | WO 2015/021270 | 2/2015 |
| WO | WO 2016/003485 | 1/2016 |
| WO | WO 2016/054939 | 4/2016 |
| WO | WO 2016/145290 | 9/2016 |
| WO | WO 2018/015544 | 1/2018 |
| WO | WO 2018/191715 | 10/2018 |
| WO | WO 2012/012779 | 1/2019 |

OTHER PUBLICATIONS

Dicarlo, et al., "Genome engineering in *Saccharomyces cervisiae* using CRISPR-Case systems", Nucleic Acids Research, 41(7):4336-43 (2013).

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial.Immunity", Science, 337:816-20 (2012).

Verwaal, et al., "CRISPR/Cpfl enables fast and simple genome editing of *Saccharamyces cerevisiae*", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Dong, "Establishment of a highly efficient virus-inducible CRISPR/Cas9 system in insect cells," Antiviral Res., 130:50-7(2016).

Epinat et al., "A novel engineered meganuclease induces homologous recombination in eukaryotic cells, e.g., yeast and mammalian cells", Nucleic Acids Research, 31(11): 2952-2962.

Farasat et al., "A Biophysical Model of CRISPR/Cas9 Activity for Rational Design of Genome Editing and Gene Regulation," PLoS Comput Biol., 29:12(1):e1004724 (2016).

(56) References Cited

OTHER PUBLICATIONS

Liu et al., "A chemical-inducible CRISPR-Cas9 system for rapid control of genome editing", Nature Chemical Biology, 12:980-987(2016).
Adamo, et al., "Flow-through comb electroporation device for delivery of macromolecules", Analytical Chemistry, 85(3):1637-41 (2015).
International Search Report and Written Opinion for International Application No. PCT/US2018/040519, dated Sep. 26, 2018, p. 1-8.
International Search Report and Written Opinion for International Application No. PCT/US2018/053670, dated Jan. 3, 2019, p. 1-13.
International Search Report and Written Opinion for International Application No. PCT/US2018/053671, dated Nov. 23, 2018, p. 1-12.
International Search Report and Written Opinion for International Application No. PCT/US2019/023342, dated Jun. 6, 2019, p. 1-12.
International Search Report and Written Opinion for International Application No. PCT/US2019/026836, dated Jul. 2, 2019, p. 1-10.
International Search Report and Written Opinion for International Application No. PCT/US2019/030085, dated Jul. 23, 2019, p. 1-14.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication for U.S. Appl. No. 16/024,831, dated Feb. 12, 2019, p. 1-37.
NonFinal Office Action for U.S. Appl. No. 16/399,988, dated Jul. 31, 2019, p. 1-20.
First Office Action Interview Pilot Program Pre-Interview Communication for U.S. Appl. No. 16/454,865 dated Aug. 16, 2019, p. 1-36.
International Search Report and Written Opinion for International Application No. PCT/US2018/053608, dated Dec. 13, 2018, p. 1-9.
International Search Report and Written Opinion for International Application No. PCT/US19/46515, dated Oct. 28, 2019, p. 1-11.
International Search Report and Written Opinion for International Application No. PCT/US19/49735, dated Nov. 18, 2019, p. 1-13.

* cited by examiner

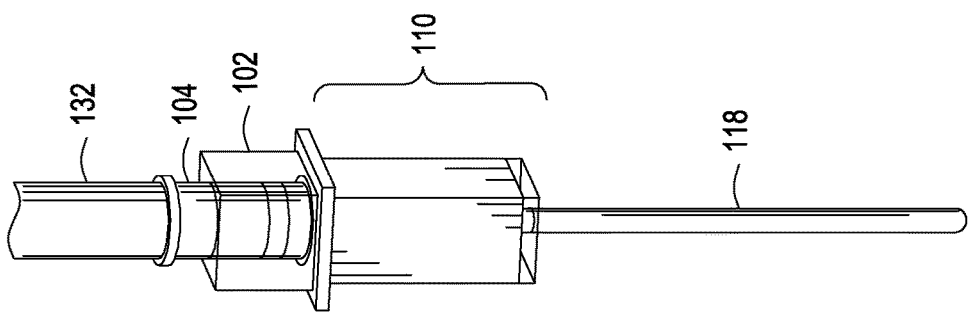
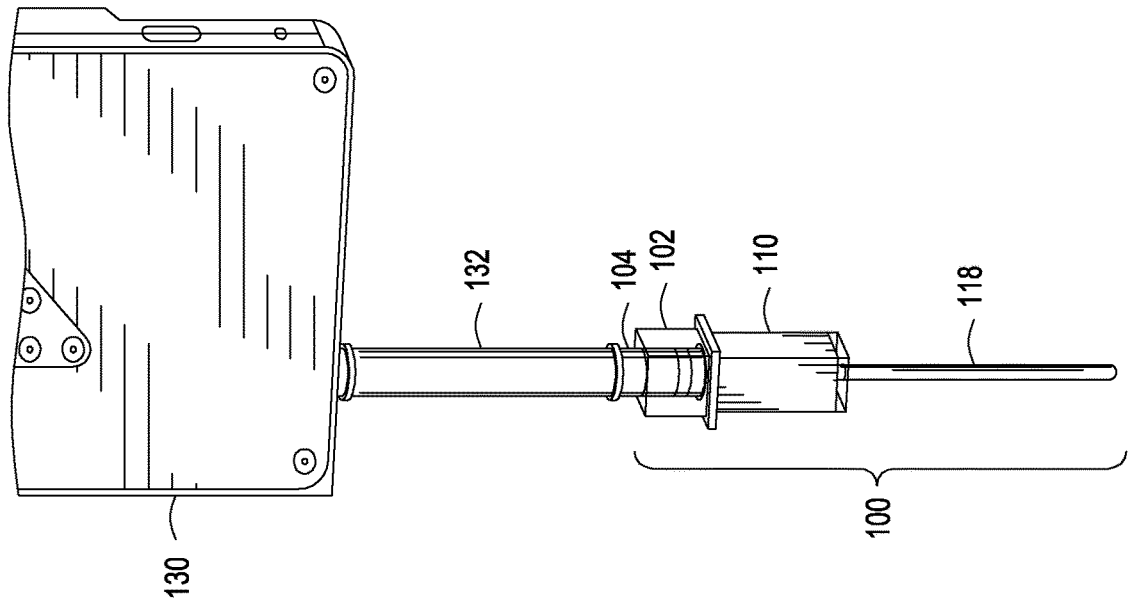
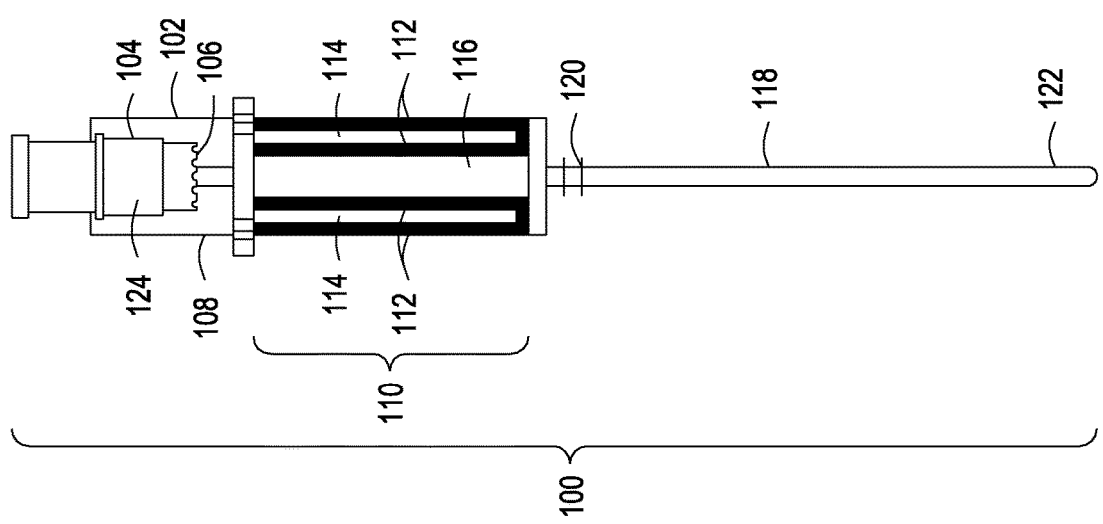

ELECTROPORATION CUVETTES FOR AUTOMATION

CROSS REFERENCE TO RELATED APPLICATIONS

The present application is a continuation of U.S. Ser. No. 16/109,156, filed Aug. 22, 2018, entitled "Electroporation Cuvettes for Automation", now U.S. Pat. No. 10,738,327; which claims the benefit of priority to U.S. Provisional Patent Application No. 62/551,069, filed Aug. 28, 2017, and is incorporated by reference.

FIELD OF THE INVENTION

The present disclosure relates to an electroporation device that may include many electroporation units and electroporation systems that can be used in an automated environment, e.g., as one station or module in a multi-station or multi-module cell processing environment.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

A cell membrane constitutes the primary barrier for the transport of molecules and ions between the interior and the exterior of a cell. Electroporation, also known as electropermeabilization, substantially increases the cell membrane permeability in the presence of a pulsed electric field. The technique is more reproducible, universally applicable, and efficient than other physical, biological or chemical techniques for transforming and transfecting cells.

Conventional electroporation is typically conducted by exerting short electric pulses of defined intensity and duration to a cuvette equipped with embedded electrodes. The electrodes are commonly fabricated out of aluminum (Al), stainless-steel, platinum (Pt) or graphite, and arranged in a parallel manner. A pulse generator such as special capacitor discharge equipment is required to generate the high voltage pulses. By tuning the electric parameters, electroporation efficiency and cell viability can be optimized.

Although traditional electroporation systems have been widely used, traditional systems require a high voltage input and suffer from adverse environmental conditions such as electric field distortion, local pH variation, metal ion dissolution and excess heat generation, often resulting in low electroporation efficiency and/or cell viability.

Accordingly, there is a need in the art for an electroporation device that predictably and reproducibly electroporates a variety of cell types, can be used with off-the-shelf liquid handling devices such as air displacement pipettes, and that can be used as part of one system in a multi-system automated cell processing environment. Additionally, there is a need in the art for an electroporation device that can electroporate many cell samples in parallel. The disclosed electroporation devices and electroporation systems address these needs.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides an electroporation device comprising an electroporation cuvette with an integrated tube or "sipper" at the bottom for cell sample input and output. The electroporation cuvette of the electroporation unit is configured to allow for integration into an electroporation device for automation, such that the electroporation device may be used as part of a larger system where transfection or transformation of target cells is one step of a series of processes or steps.

In specific aspects, the invention provides an automated electroporation device having one to many electroporation units comprising an electroporation cuvette coupled with an adapter or engagement member at the top that is configured for engagement with liquid handling instrumentation, and a "sipper" conduit at the bottom for sample intake and output. In some specific aspects, the electroporation device is adapted to engage with an off-the-shelf pipetting instrument, e.g., an air displacement pipette. In other specific aspects, the electroporation devices are adapted to engage with a pump, e.g., an air displacement pump or peristaltic pump. In some embodiments, the electroporation device may comprise a single electroporation unit configured to be used with, e.g., a single channel pipette as part of an automated system. In other embodiments, the electroporation device comprises two to many electroporation units configured to be used with a multi-channel pipetting instrument which also may be part of an automated system. That is, the electroporation device may be a module used as part of a system including a pipette and an electroporation station, and this electroporation system may be one module in a multi-module system used for cell processing. For example, the electroporation module may be integrated in a multi-module system for protein production, where cells are transformed with an expression vector, the cells are cultured following transformation, and expression of a protein or proteins of interest are induced in the system. In another example, the electroporation module can be integrated into an automated multi-module system for cell editing, including recursive cell editing.

In one embodiment, the specification describes an electroporation module for electroporating cell samples comprising a pipetting device; and an electroporation device, wherein the electroporation device comprises: a housing that houses an engagement member and a filter; an electroporation cuvette comprising an electroporation chamber defined by walls and at least two electrodes wherein the electrodes are parallel to one another and wherein the electroporation chamber is in fluid communication with the filter; and a sipper in fluid communication with the electroporation chamber, wherein the sipper is configured for intake and output of the cells and/or material to be electroporated in the vessel; and wherein the engagement members of the units are configured such that the electroporation device can engage with the pipetting device. In some aspects the electroporation module further comprises an electroporation station; and the electroporation module further comprises a first reservoir disposed between the electroporation chamber and the filter, wherein the first reservoir is in fluid communication with the electroporation chamber; and/or in some aspects the electroporation device may also further comprise a second reservoir disposed between the filter and the engagement member.

In some aspects of this embodiment, the electroporation device of the electroporation system is configured to electroporate a cell sample having a volume of 1 µl to 2 ml, 50 µl to 1 ml, 100 µl to 500 µl, or 200 µl to 400 µl.

In some aspects, the cells in the cell sample are mammalian cells, plant cells, yeast cells, or bacteria cells, and in some aspects, the material to be electroporated into the cells comprises nucleic acids, peptides, proteins, hormones, cytokines, chemokines, drugs, or drug precursors; most particularly, the material to be electroporated into the cells may comprise nucleic acids.

In some aspects, the engagement member and/or the housing of the electroporation device comprises silicone, resin, polyvinyl chloride, polyethylene, polyamide, polyethylene, polypropylene, acrylonitrile butadiene, polycarbonate, polyetheretheketone (PEEK), polysulfone or polyurethane, or co-polymers of these polymers. In some aspects, the walls of the electroporation chamber comprise glass, crystal styrene or cyclic olephin co-polymers; and the electrodes of the electroporation chamber comprise aluminum, copper, titanium, aluminum, brass, silver, rhodium, gold or platinum, or graphite.

One aspect of the electroporation module provides that the pipetting device is an air displacement pipette.

In addition, one aspect provides that the electroporation module is an automated electroporation cell module, and in some aspects, the automated electroporation cell module is one module in an automated multi-system cell processing system.

In some aspects, the electroporation module comprises one or more multi-channel air displacement pipettes and one or more electroporation stations; and in some aspects of the electroporation system the electroporation device is a multi-unit electroporation device, the pipetting device is a multi-channel air displacement pipette, and the electroporation module further comprises a multi-unit electroporation station. Additional aspects provide that the electroporation module is automated.

In addition, one embodiment described provides a multi-unit electroporation device for electroporation of cell samples in parallel, the cell sample comprising cells and a material to be electroporated into the cells, the electroporation device comprised of at least two electroporation units wherein an electroporation unit comprises: a housing that houses an engagement member and a filter; an electroporation cuvette comprising an electroporation chamber defined by walls and at least two electrodes, wherein the electrodes are parallel to one another and wherein the electroporation chamber is in fluid communication with the filter; and a sipper in fluid communication with the electroporation chamber, wherein the sipper is configured for intake and output of the cell sample.

In some aspects, the units of the multi-unit electroporation device further comprise a first reservoir disposed between the electroporation chamber and the filter, wherein the first reservoir is in fluid communication with the electroporation chamber; and/or a second reservoir disposed between the filter and the engagement member.

In some aspects one or more electroporation units are configured to electroporate a cell sample having a volume of 1 µl to 2 ml, 50 µl to 1 ml, 100 µl to 500 µl, or 200 µl to 400 µl.

In some aspects, the cells to be electroporated in the cell sample are mammalian cells, plant cells, yeast cells, or bacteria cells and in some aspects, the material to be electroporated into the cells comprises nucleic acids, peptides, proteins, hormones, cytokines, chemokines, drugs, or drug precursors.

Often, the engagement member is configured to engage with a multi-channel pipette, and in some aspects, the multi-channel pipette is an air displacement pipette.

In some aspects, there is provided a multi-unit electroporation module comprising the multi-unit electroporation device, a multi-channel air displacement pipette, and a multi-channel electroporation station, and in some circumstances the multi-unit electroporation module is automated. Further, the automated multi-unit electroporation module may be one module in an automated multi-module cell processing system.

Often the electroporation units are arranged linearly, and adjacent electroporation units share an electrode. In some aspects, the electroporation module comprises at least 32 electroporation units, at least 64 electroporation units or at least 96 electroporation units. In addition, the multi-module cell processing system comprises one or more of the multi-unit electroporation devices.

Additionally, there is provided a multi module automated cell system comprising the electroporation module.

In yet another embodiment, there is provided a method for electroporating a cell sample using the electroporation module, comprising the steps of moving the electroporation device to engage with a vessel comprising a cell sample; sipping the cell sample from the vessel through the sipper of the electroporation device into the electroporation chamber; moving the electroporation device to the electroporation station; engaging the electroporation device with the electroporation station; electroporating the cell sample in the electroporation chamber of the electroporation device; moving the electroporation device to a position to dispense the electroporated cell sample into a vessel comprising recovery medium; and dispensing the cell sample from the electroporation chambers through the sippers and into the vessels comprising recovery medium.

Some aspects of this embodiment further comprise the steps of ejecting the electroporation device from the pipetting device, and in some aspects, the method further comprises repeating the moving, sipping, moving, engaging, electroporating, moving, dispensing and ejecting steps.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1 depicts an exemplary single-unit electroporation device consistent with the disclosed embodiments.

FIG. 2A depicts a single-unit electroporation device engaged with an exemplary embodiment of liquid handling instrumentation. FIG. 2B illustrates a close-up of the single-unit electroporation device engaged with the embodiment of liquid handling instrumentation shown in FIG. 2A.

It should be understood that the drawings are not necessarily to scale, and that like reference numbers refer to like features.

DETAILED DESCRIPTION

Figure 4:
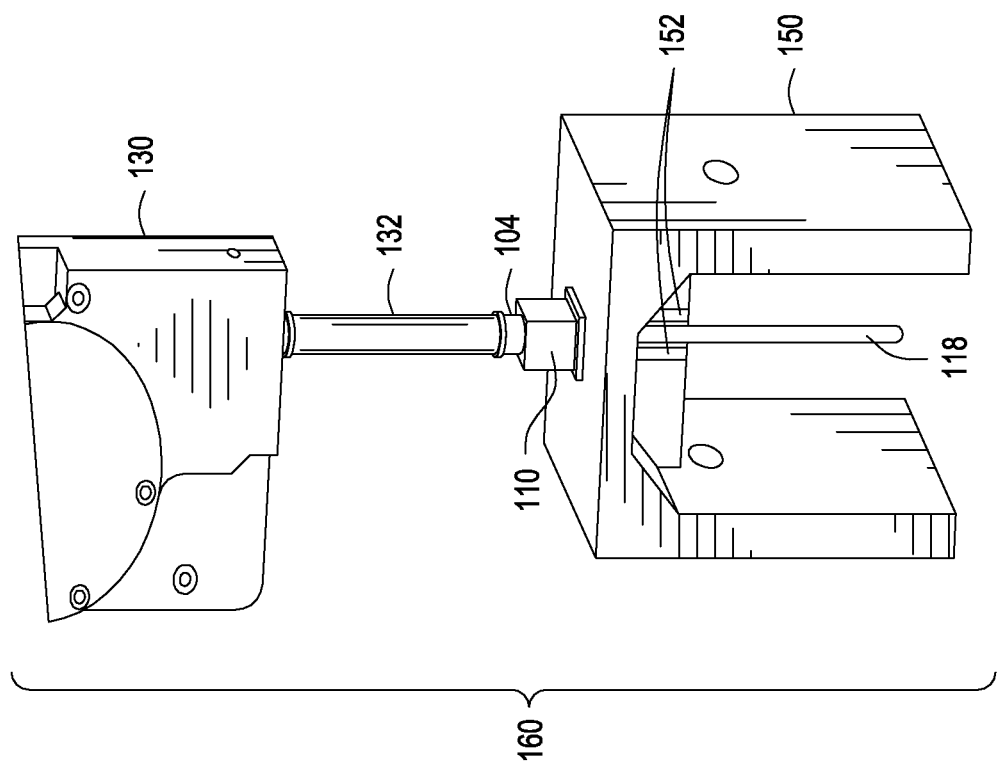
FIG. 4 depicts a single-unit electroporation device engaged with one embodiment of liquid handling instrumentation as well as engaged with one embodiment of a single-unit electroporation station.

The practice of the techniques described herein may employ, unless otherwise indicated, conventional techniques and descriptions molecular biology (including recombinant techniques), cell biology, biochemistry, and genetic engineering technology, which are within the skill of those who practice in the art. Such conventional techniques and descriptions can be found in standard laboratory manuals such as Green and Sambrook, *Molecular Cloning: A Laboratory Manual.* 4th, ed., Cold Spring Harbor Laboratory Press, Cold Spring Harbor, N.Y., (2014); *Current Protocols in Molecular Biology*, Ausubel, et al. eds., (2017); Neumann, et al., *Electroporation and Electrofusion in Cell Biology*, Plenum Press, New York, 1989; and Chang, et al., *Guide to Electroporation and Electrofusion*, Academic Press, California (1992), all of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

Electroporation is a widely-used method for permeabilization of cell membranes that works by temporarily generating pores in the cell membranes with electrical stimulation. The applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells. During a typical electroporation procedure, cells are suspended in a buffer or medium that is favorable for cell survival. For bacterial cell electroporation, low conductance mediums, such as water, glycerol solutions and the like, are often used to reduce the heat production by transient high current. The cells and material to be electroporated into the cells (collectively "the cell sample") is then placed in a cuvette embedded with two flat electrodes for an electrical discharge. For example, Bio-Rad (Hercules, Calif.) makes the GENE PULSER XCELL™ line of products to electroporate cells in cuvettes. Traditionally, electroporation requires high field strength.

Generally speaking, microfluidic electroporation—using cell suspension volumes of less than approximately 20 ml and as low as 1 µl and typically in the 50-500 µL range— allows more precise control over a transfection or transformation process and permits flexible integration with other cell processing tools compared to bench-scale electroporation devices. Microfluidic electroporation thus provides unique advantages for, e.g., single cell transformation, processing and analysis; multi-unit electroporation device configurations; and integrated multi-module cell systems for processing and analysis.

The present disclosure provides electroporation devices, electroporation systems and methods that achieve high efficiency cell electroporation with low toxicity where the electroporation devices and systems can be integrated with other automated cell processing tools. The electroporation device of the disclosure allows for multiplexing where two to many electroporation units are constructed and used in parallel, and the electroporation device allows for particularly easy integration with robotic liquid handling instrumentation. Such automated instrumentation includes, but is not limited to, off-the-shelf automated liquid handling systems from Tecan (Mannedorf, Switzerland), Hamilton (Reno, Nev.), Beckman Coulter (Fort Collins, Colo.), etc.

In specific embodiments of the electroporation devices of the disclosure, the transformation results in greater than 30% viable cells after electroporation, and even greater than 35%, 40%, 45%, 50%, 55%, 60%, 70%, 75%, 80%, 85%, 90%, or even 95% viable cells following transformation, depending on the cell type and the nucleic acids being introduced into the cells.

The electroporation unit(s) of the electroporation device comprises a housing with an electroporation chamber that forms the body of the container, a first electrode and a second electrode configured to engage with an electric pulse generator in an electroporation station and where the electrodes define the chamber to hold the cell sample to be electroporated, an engagement member that allows the electroporation unit to engage with a pipette or pump, a "sipper" for intake of the cells and the material to be electroporated into the cells (collectively the "cell sample") and to dispense the electroporated cell sample into, e.g., recovery medium, and a filter between the engagement member and the electroporation chamber. In certain embodiments, the electroporation devices are autoclavable and/or disposable.

FIG. 1 depicts an exemplary single-unit electroporation device consistent with the disclosed embodiments. The single-unit electroporation device 100 comprises from top to bottom, a housing 102 that encloses an engagement member 104 configured to engage with a pipette such as an automatic air displacement pipette (not shown), and a filter 106. In addition to the housing 102, there is an electroporation cuvette 110 portion of the electroporation unit comprising electrodes 112, and walls 114 of the electroporation chamber 116. Additionally, between the filter 106 and the electroporation chamber 116 may be placed a first optional reservoir 108, which is in fluid communication with electroporation chamber 116 and provides an empty repository for any cell sample that may be taken in past the electroporation chamber 116. In addition, the electroporation unit may comprise another optional reservoir 124, which is in fluid communication with the first reservoir 108 (through filter 106) and is placed between filter 106 and engagement member 104 to protect the pipette from any liquids that may make it past the filter 106. In fluid communication with and coupled to the electroporation chamber 116 is sipper 118, having an end proximal 120 to the electroporation chamber 116 and an end distal 122 from the electroporation chamber 116. It is the distal end 122 of the sipper that allows for uptake and dispensing of the cell sample from the electroporation device 100.

Electroporation units of the electroporation device may be configured to electroporate cell sample volumes of between 1 μl to 20 ml although most typically in the 10 μL to 1 mL range, or the 50 μL to 500 μL range. The approximate dimensions of the various components of the disclosed electroporation units are given in Table 1, and dimensions, of course, will vary depending on the volume of the cell sample and the container(s) that are used to contain the cells and/or material to be electroporated.

tures or portions thereof can be created through various techniques, e.g., injection molding, creation of structural layers that are fused, etc.

Filter 106 can be fashioned from any suitable and preferably inexpensive material, including porous plastics, hydrophobic polyethylene, cotton, or glass fiberse. Sipper 118 can be made from plastics such as polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers, glass (such as a glass capillary), and metal tubing such as aluminum, stainless steel, or copper. Exemplary materials include crystal styrene and cyclic olephin co-polymers. The engagement member 104 is configured to have a dimension that is compatible with the liquid handling device used in the electroporation system. The components of the electroporation devices may be manufactured separately and then assembled, or certain components of the electroporation devices may be manufactured or molded as a single entity, with other components added after molding. For example, the sipper, electroporation walls, and housing may be manufactured or molded as a single entity, with the electrodes, filter, engagement member later added to the single entity to form the electroporation unit. Similarly, the electroporation walls and housing may be manufactured as a single entity, with the sipper, electrodes, filter, engagement member added to the electroporation unit after molding.

The electrodes 112 can be formed from any suitable metal, such as copper, titanium, aluminum, brass, silver, rhodium, gold or platinum, or graphite. An applied electric field can destroy electrodes made from of metals like aluminum. If a multiple use electroporation device is desired—as opposed to a disposable, one-use device—the electrode plates can be coated with metals resistant to electrochemical corrosion. Conductive coatings like noble metals, e.g., gold, can be used to protect the electrode plates. For example, the electroporation cuvette may comprise a

TABLE 1

| COMPONENT | WIDTH (mm) RANGE | HEIGHT (mm) RANGE | VOLUME (μl) RANGE | WIDTH (mm) RANGE | HEIGHT (mm) RANGE | VOLUME (μl) RANGE | WIDTH (mm) RANGE | HEIGHT (mm) RANGE | VOLUME (μl) RANGE |
|---|---|---|---|---|---|---|---|---|---|
| Electroporation chamber 116 | 0.01-100 | 1-5000 | 1-20000 | 0.03-50 | 50-2000 | 500-10000 | 0.05-30 | 2-500 | 25-4500 |
| First reservoir 108 | 0.1-150 | 0.1-250 | 0.5-10000 | 0.3-100 | 30-150 | 20-4000 | 0.5-100 | 0.5-100 | 5-2000 |
| Second reservoir 124 | 0.1-250 | 0.2-1000 | 0.1-2500 | 0.1-150 | 50-400 | 1-1000 | 0.2-100 | 0.5-200 | 2-600 |
| Filter 106 | 0.2-500 | 0.2-500 | 1-3000 | 0.3-250 | 20-200 | 50-2500 | 0.5-150 | 0.2-80 | 10-2000 |
| Sipper 118 | 0.02-2000 | 0.25-2000 | 1-2000 | 0.02-1250 | 250-1500 | 1.5-1500 | 0.02-10 | 4.0-1000 | 2.5-1000 |

Housing 102 and engagement member 104 of the electroporation units can be made from any suitable material, including silicone, resin, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Similarly, the walls 112 of the electroporation chamber may be made of any suitable material including silicone, resin, glass, glass fiber, polyvinyl chloride, polyethylene, polyamide, polyethylene, polypropylene, acrylonitrile butadiene, polycarbonate, polyetheretheketone (PEEK), polysulfone and polyurethane, co-polymers of these and other polymers. Exemplary materials include crystal styrene and cyclic olephin co-polymers. These strucfirst metal electrode and a second metal electrode made from titanium covered with a layer of gold.

In one embodiment, the distance between the electrodes may be between 0.3 mm and 50 mm. In another embodiment, the distance between the electrodes may be between 1 mm and 20 mm, or 1 mm to 10 mm, or 2 mm to 5 mm. The inner diameter of the electroporation chamber may be between 0.1 mm and 10 mm. Preferably, the first metal electrode and the second metal electrode are separated by a distance of 2-4 mm in a parallel arrangement with variations in distance less than +/−20 μm. To avoid different field intensities between the electrodes, the electrodes should by arranged in parallel with a constant distance to each other over the whole surface of the electrodes. Furthermore, the surface of the electrodes should be as smooth as possible without pin holes or peaks. Electrodes having a roughness Rz of 1 to 10 μm are preferred. In another embodiment of the invention, the electroporation device comprises at least one additional electrode which applies a ground potential to, e.g., the sipper portion of the electroporation device. Additionally, in a multi-unit electroporation device, the electrodes may either be independent, standalone electrodes. Alternatively, the multi-unit electroporation device may include electrodes arranged such that electroporation cuvettes in adjacent electroporation units share electrodes, as discussed infra in relation to FIG. 5. Such multi-unit electroporation devices may comprise, e.g., 2 or more electroporation units, 4 or more electroporation units, 8 or more electroporation units, 16 or more electroporation units, 32 or more electroporation units, 48 or more electroporation units, 64 or more electroporation units, or even 96 or more electroporation units preferably in an automated module and system.

Electroporation chambers of various shapes are convenient to manufacture and use, and an electroporation chamber for use with the disclosed electroporation device may use any suitable shape. For example, a rectangular container, a square container, a cylindrical container, a conical container, or container with other shapes are suitable.

FIG. 2A depicts a single-unit electroporation device engaged with one embodiment of liquid handling instrumentation. The single-unit electroporation device comprises from top to bottom, a housing 102 that encloses an engagement member 104 configured to engage with the shaft 132 of a pipette 130 such as an automatic air displacement pipette. Coupled to the housing 102, there is an electroporation cuvette 110 portion of the electroporation device 100. The electroporation chamber (not labeled, but contained within the interior of the electroporation cuvette 110) is in fluid communication with sipper 118.

FIG. 2B illustrates a close-up of the single-unit electroporation device engaged with the embodiment of liquid handling instrumentation shown in FIG. 2A. In FIG. 2B, the pipette is not shown; however, the shaft 132 of the pipette is shown engaged with the engagement member 104 within housing 102. Also shown is filter 106, electroporation cuvette 110 (which as shown in FIG. 1 as comprising at least two electrodes, and walls defining an electroporation chamber, none of which are labeled in FIG. 2B). Sipper 118 is coupled to and in fluid communication with the electroporation chamber within the electroporation cuvette 110.

The pipettes that may be employed with the disclosed electroporation device include air displacement pipettes, which use air displacement to aspirate and dispense fluids, and in particular automated air displacement pipettes used in robotic systems. For example, the electroporation device of the disclosure can be integrated with Tecan's Cavro air displacement pipettor (ADP), or the Hamilton Z-Excursion Universal Sampler (ZEUS), a fully automated, self-contained pipetting module. In addition, the Beckman Coulter Biomek i5 and i7 Automated Workstations utilize piston-driven air displacement pipettes to handle volumes of liquid in the microliter scale pipettes. Air displacement pipettes offer accurate pipetting performance from 1 to 1,000 When used with the disclosed electroporation device, the pipette will often comprise an ejector system that can automatically eject a used electroporation device after the electroporated cells have been deposited into the recovery medium.

The electroporation devices of the present disclosure can be configured to be multi-unit electroporation devices that comprise two to many electroporation units in parallel so that they can be used, e.g., with off-the-shelf multi-channel pipettes; for example, a multi-unit electroporation device may be configured with 4 or 6 electroporation units in parallel to be used with a 4- or 6-channel pipette device for input or output of cells and/or reagents, e.g., for use with a 24-well culture plate; a multi-unit electroporation device may be configured with 8 electroporation units in parallel in parallel to be used with an 8-channel pipette device for input and/or output of cells or reagents, e.g., for use with a 48- or 96-well culture plate; a multi-unit electroporation device may be configured with 12 electroporation units in parallel to be used with a 12-channel pipette device for input or output of cells and/or reagents, e.g., for use with a 128-well culture plate; or any other desired configuration.

In lieu of a pipette arrangement where a pipette is used to both intake and evacuate a cell sample into the electroporation cuvette (including the disclosed embodiment of an automated air displacement pipette), a peristaltic pump or a vacuum pump may be employed. Accordingly, the electroporation chamber is in communication with a pump that intakes the cell sample into the electroporation chamber and evacuates the cells after electroporation into a tube containing recovery medium.

Figure 3:
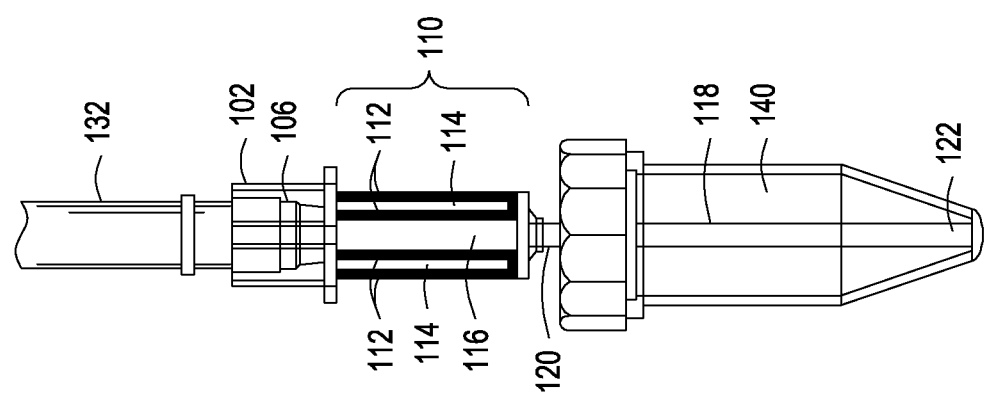
FIG. 3 illustrates a close-up of the single-unit electroporation device engaged with the liquid handling instrumentation shown in FIG. 2B, further engaged with a vessel or tube from which the electroporation device "sips" the cells and material to be electroporated.

FIG. 3 illustrates a close-up of the single-unit electroporation device engaged with the liquid handling instrumentation shown in FIG. 2B, further engaged with a tube from which the electroporation device "sips" the cells and material to be electroporated. In FIG. 3 like in FIG. 2B, the pipette is not shown; however, the shaft 132 of a pipette is shown, engaged with the engagement member 104 within housing 102 of the single-unit electroporation device. Also shown is filter 106, electroporation cuvette 110 (which as shown in FIG. 1 as comprising at least two electrodes, and walls defining an electroporation chamber, none of which are labeled in FIG. 3). Sipper 118 is coupled to and in fluid communication with the electroporation chamber within the electroporation cuvette 110 at its proximal end 120, and is engaged with tube 140, where the distal end 122 of sipper 118 is fully immersed in tube 140. In one exemplary embodiment, cells and a material to be electroporated into the cells (collectively, a "cell sample") are contained in tube 140. Alternatively, the cells and the material to be electroporated into the cells are contained in different tubes and the sipper 118 engages with two (or more) different tubes to fill the electroporation chamber of the electroporation cuvette with a cell sample.

The cells that may be electroporated with the disclosed electroporation devices include mammalian cells (including human cells), plant cells, yeasts, other eukaryotic cells, bacteria, archaea, and other cell types. The volume of the cell sample that can be electroporated with the disclosed electroporation devices is from 1 μl to 2 ml, or 50 μl to 1 ml, or 100 μl to 500 μl, or 200 μl to 400 μl.

The medium or buffer used to suspend the cells and material to be electroporated into the cells for the electroporation process may be any suitable medium or buffer, such as MEM, DMEM, IMDM, RPMI, Hanks', PBS and Ringer's solution. For electroporation of most eukaryotic cells, the medium or buffer usually contains salts to maintain a proper osmotic pressure. The salts in the medium or buffer also render the medium conductive. For electroporation of very small prokaryotic cells such as bacteria, sometimes water is used as a low conductance medium to allow a very high electric field strength. In that case, the charged molecules to be delivered still render water based medium more conductive than the lipid-based cell membranes and the medium may still be roughly considered as conductive especially compared to cell membranes.

The compound to be electroporated into the cells of choice can be any compound known in the art to be useful for electroporation, such as nucleic acids, oligonucleotides, polynucleotides, DNA, RNA, peptides, proteins and small molecules like hormones, cytokines, chemokines, drugs, or drug precursors.

FIG. 4 depicts an exemplary single-unit electroporation device engaged with one embodiment of liquid handling instrumentation (e.g., an automated air displacement pipette) as well as engaged with one embodiment of a single-unit electroporation station where collectively these components—electroporation device, liquid handling instrumentation, and electroporation station—are an "electroporation module" 160. Also seen is electroporation cuvette 110 of the single-unit electroporation device that has been inserted into a hole or opening within electroporation station 150. The hole in electroporation station 150 is configured to precisely engage with the electroporation cuvette 110, such that the electrodes (not labeled) of electroporation cuvette 110 engage with the electrical contacts 152 of the electroporation station 150. Also seen is sipper 118.

The electroporation station 150 generates the electrical pulse to electroporate the cells via contacts 152, where the contacts are in electrical communication with the electrodes of the electroporation cuvette 110. The electroporation station may generate one or several different pulse forms such as a sequence of high energy pulses to open the pores of the cell membrane, and a series of lower energy pulses to transport the material to be electroporated into the cells. There are many different pulse forms that may be employed with the electroporation cuvette, including exponential decay waves, square or rectangular waves, arbitrary wave forms, or a selected combination of wave forms. The pulse forms for electroporation may be predetermined based on cell type, the size and configuration of the electroporation chamber and of the electrodes therein, and/or other parameters. The electroporation station thus preferably comprises on-board electronics to deliver the predetermined pulses for electroporation. One type of common pulse form is the exponential decay wave, typically made by discharging a loaded capacitor to the cell sample. The exponential decay wave can be made less steep by linking an inductor to the cell sample so that the initial peak current can be attenuated. When multiple waveforms in a specified sequence are used, they can be in the same direction (direct current) or different directions (alternating current). Using alternating current can be beneficial in that two topical surfaces of a cell instead of just one can be used for molecular transport, and alternating current can prevent electrolysis. The pulse generator can be controlled by a digital or analog panel.

It is important to use voltage sufficient for achieving electroporation of material into the cells, but not too much voltage as too much power will decrease cell viability. For example, to electroporate a suspension of a human cell line, 200 volts is needed for a 0.2 ml sample in a 4 mm-gap cuvette with exponential discharge from a capacitor of about 1000 g. However, if the same 0.2 ml cell suspension is placed in a longer container with 2 cm electrode distance (5 times of cuvette gap distance), the voltage required would be 1000 volts, but a capacitor of only 40 µF (1/25 of 1000 µF) is needed because the electric energy from a capacitor follows the equation of:

$$E = 0.5 U^2 C$$

where E is electric energy, U is voltage and C is capacitance. Therefore, a high voltage pulse generator is easy to manufacture because it needs a much smaller capacitor to store a similar amount of energy. Similarly, it would not be difficult to generate other wave forms of higher voltages.

Figure 5:
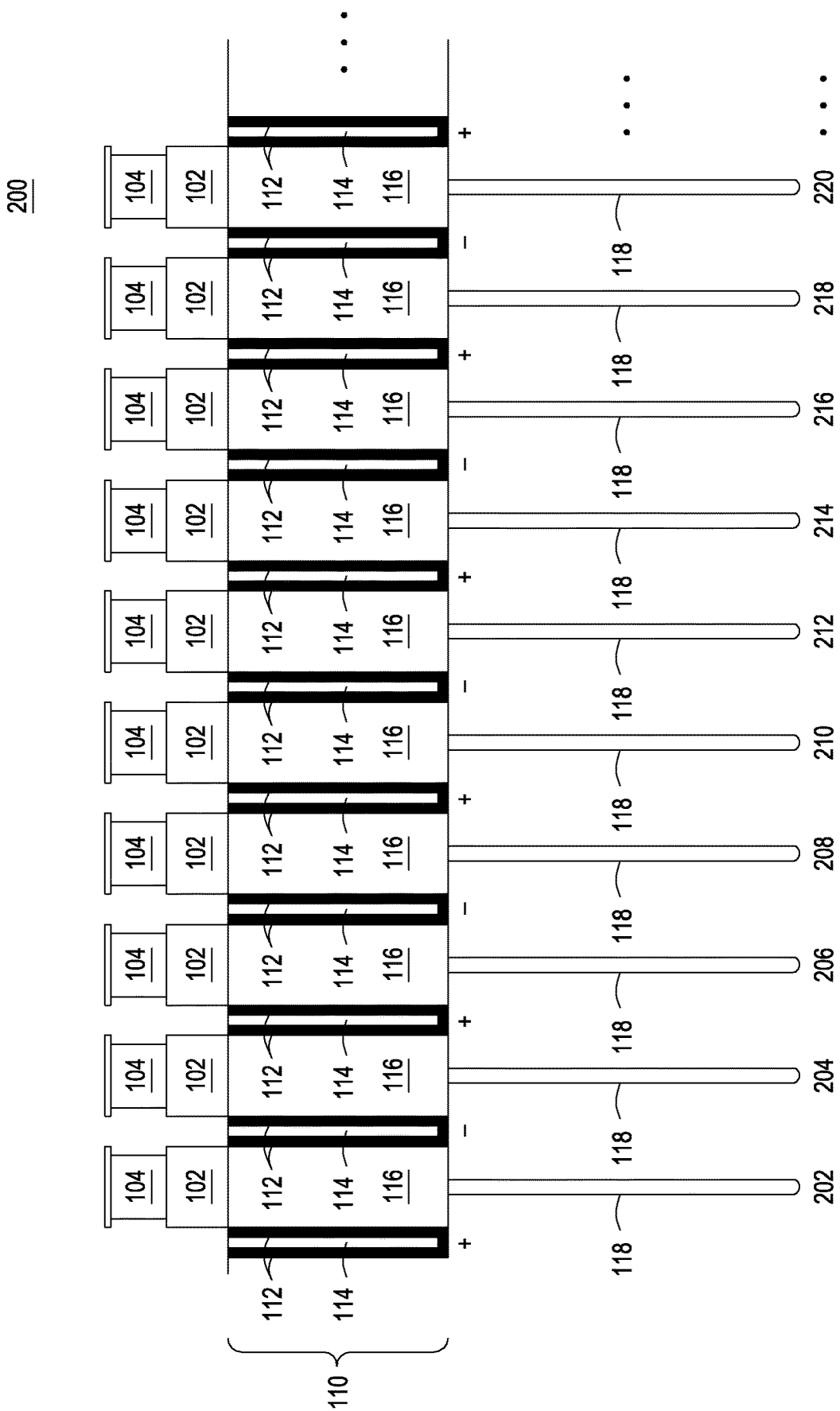
FIG. 5 illustrates a multi-unit electroporation device consistent with the disclosed embodiments.

FIG. 5 illustrates a multi-unit electroporation device 200 consistent with the disclosed embodiments. In this embodiment, electroporation units 202, 204, 206, 208, 210, 212, 214, 216, 218, 220 of the electroporation device 200 are arranged linearly, in parallel. The electroporation unit comprises an electroporation cuvette 110, coupled with a housing 112 comprising an adapter or engagement member 104 at the top that is configured for engagement with liquid handling instrumentation, and a "sipper" 118 conduit at the bottom for sample intake and output. In this embodiment where the electroporation units are arranged linearly, adjacent electroporation cuvettes share electrodes, for example, such that the negative electrode of electroporation units 202 and 204 is shared, the positive electrode of electroporation units 204 and 206 is shared, that the negative electrode of electroporation units 206 and 208 is shared, and so on. The multi-unit electroporation device is configured—and the engagement members 104 of the electroporation unit 202, 204, etc. are configured—to engage with, e.g., the shaft of a multi-channel pipette (not shown).

Figure 6:
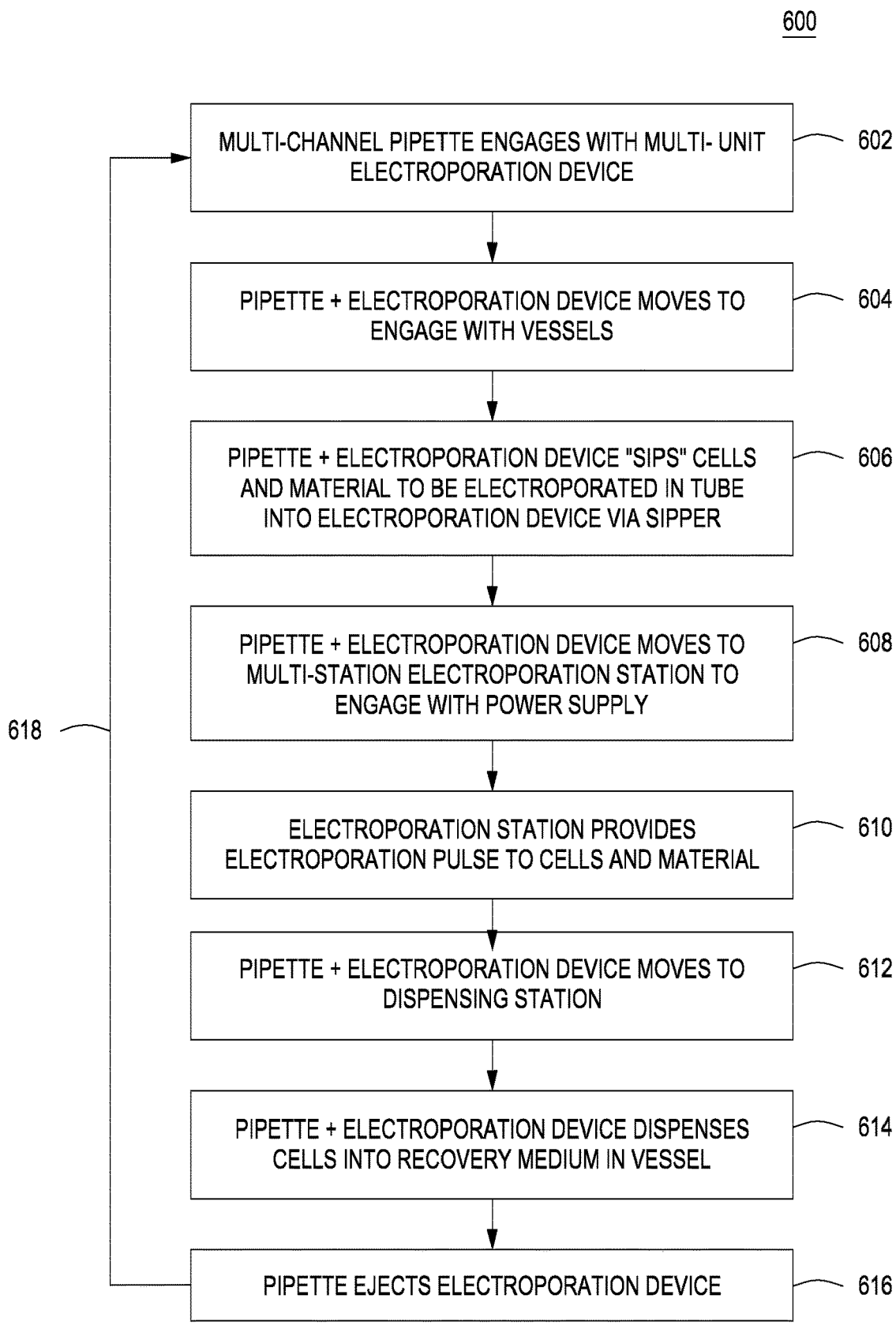
FIG. 6 is a simplified block diagram of one embodiment of a method that may be performed with the electroporation devices and electroporation systems consistent with the disclosed embodiments.

FIG. 6 is a simplified block diagram of an exemplary embodiment of a method 600 that can be performed with the electroporation device and electroporation system consistent with the disclosed embodiments. At step 602, a liquid handling device (e.g., pipette) engages with an electroporation device, such as that depicted in FIG. 1 or FIG. 5. In a robotic environment, one to many electroporation devices such as the single-unit electroporation device depicted in FIG. 1 may be available (e.g., lined up) for engagement with one or more liquid handling devices, alternatively, a multi-unit electroporation device, such as that depicted in FIG. 5, engages with a multi-channel pipette. At step 604, the combination liquid handling device and electroporation device moves to engage with a tube(s) containing, e.g., cells and material to be electroporated into the cells. Alternatively, the cells and the material to be electroporated into the cells may be in separate tubes, and the combination liquid handling device and electroporation device will take in the cells and material to be electroporated into the cells from separate tubes. The sipper component of the electroporation device then "sips" or takes up the liquid from the tube up into the electroporation chamber of the electroporation cuvette at step 606. As seen in FIGS. 1, 3, and 5, the electroporation chamber is encompassed by the walls of the electroporation chamber, and two of the walls of the electroporation chamber are adjacent to the two electrodes which are parallel to one another.

At step 608, the combination liquid handling device and electroporation device moves to engage with the electroporation station, which supplies the power to electroporate the cell sample(s) that is within the electroporation chamber of the electroporation device. The combination of the liquid handling device, electroporation device, and electroporation station is referred to herein as an electroporation module. After the electroporation cuvette of the electroporation device is firmly seated within the electroporation station such that the electrical contacts of the electroporation station are electrically engaged with the electrodes of the electroporation device, the electroporation station provides one or a series of electrical pulses to the cell sample at step 610. As discussed supra, the electrical pulses may encompass one or several different pulse forms. In many embodiments, the electroporation station comprises on-board electronics which can control the type, strength and duration of the pulse forms delivered to the cell sample in a predetermined manner. The type of electronics board used in the electroporation station may include but is not limited to, e.g., a capacity discharge board, or a voltage amplifying board. At step 612, the combination liquid handling device and electroporation device moves to a dispensing station where the electroporated cells are cleared from the device, often into recovery medium to allow the pores of the cells to close and the cell membrane to recover from the electroporation process (step 614).

Once recovered, the cells then may be used in further processing procedures such as enrichment and/or depletion of certain subsets of cells, and/or cell culturing. The further processing procedures may be performed as another part of an automated system that comprises two to many automated processes. Alternatively, a second material to be electroporated into the cells may be "sipped" and another round of electroporation pulses may be delivered to the cells with or without a recovery, washing, culturing or separation step. Once the electroporated cell sample(s) has been dispensed, the pipette ejects the electroporation device at step 616. As stated previously, in certain embodiments the electroporation device is disposable, and thus the electroporation device may be discarded. In other embodiments the electroporation devices are reusable and can be autoclaved between uses.

To electroporate more cells (i.e., different cells, more cells of the same type but with different materials to be electroporated, or additional volumes of the same cell sample), the process of filling, electroporation and clearance can be repeated (as shown by reference number 618).

The electroporation devices and electroporation modules of the invention may be a component of a broader automated cell multi-module system that can be utilized for various purposes involving the transformation and capture of live cells. For example, the electroporation device may be integrated into an automated multi-module system for protein production, where the cells are transformed with an expression vector, the cells are cultured following transformation, and the expression of a protein or proteins of interest are induced in the system. In another example, the electroporation device may be integrated into an electroporation module which is a part of an automated multi-module system for cell engineering and selection to identify the transformed cells, with the selection process occurring on the automated system. In specific aspects, the electroporation device and module can be integrated into an automated system for cell editing, including recursive cell editing. Such automated multi-module systems include but are not limited to those described, e.g., in U.S. Ser. No. 16/024,816, filed Jun. 30, 2018; U.S. Ser. No. 16/024,831, filed Jun. 30, 2018, U.S. Ser. No. 62/657,651, filed Apr. 13, 2018; and U.S. Ser. No. 62/657,654, filed May 14, 2018, all of which are incorporated by reference herein for all purposes.

The system may also include pressure sources and/or regulators that control the flow of liquids in the system and control the rate and volume of electroporation.

The electroporation devices of the disclosure can allow for a high rate of cell transformation in a relatively short amount of time. The rate of cell transformation is dependent on the cell type and the number of cells being transformed. For example, for *E. Coli*, the electroporation devices can provide a cell transformation rate of 1 to $10^{10}$ cells per second, $10^4$ to $10^7$ per second, $10^5$ to $10^8$ per second, or $10^6$ to $10^9$ per second. The electroporation devices also allow transformation of batches of cells ranging from 1 cell to $10^{10}$ cells in a single transformation procedure using the device.

The efficiency of the transformation using the electroporation devices of the disclosure can result in at least 10% of the cells being sufficiently porated to allow delivery of the biological molecule. Preferably, the efficiency of the transformation using the electroporation devices of the disclosure can result in at least 15%, 20%, 25%, 30%, 35%, 40%, 45%, 50%, 55%, 60%, 75%, 80%, 85%, 90%, 95% or greater of the cells being sufficiently porated to allow delivery of the biological molecule.

Figure 7A:
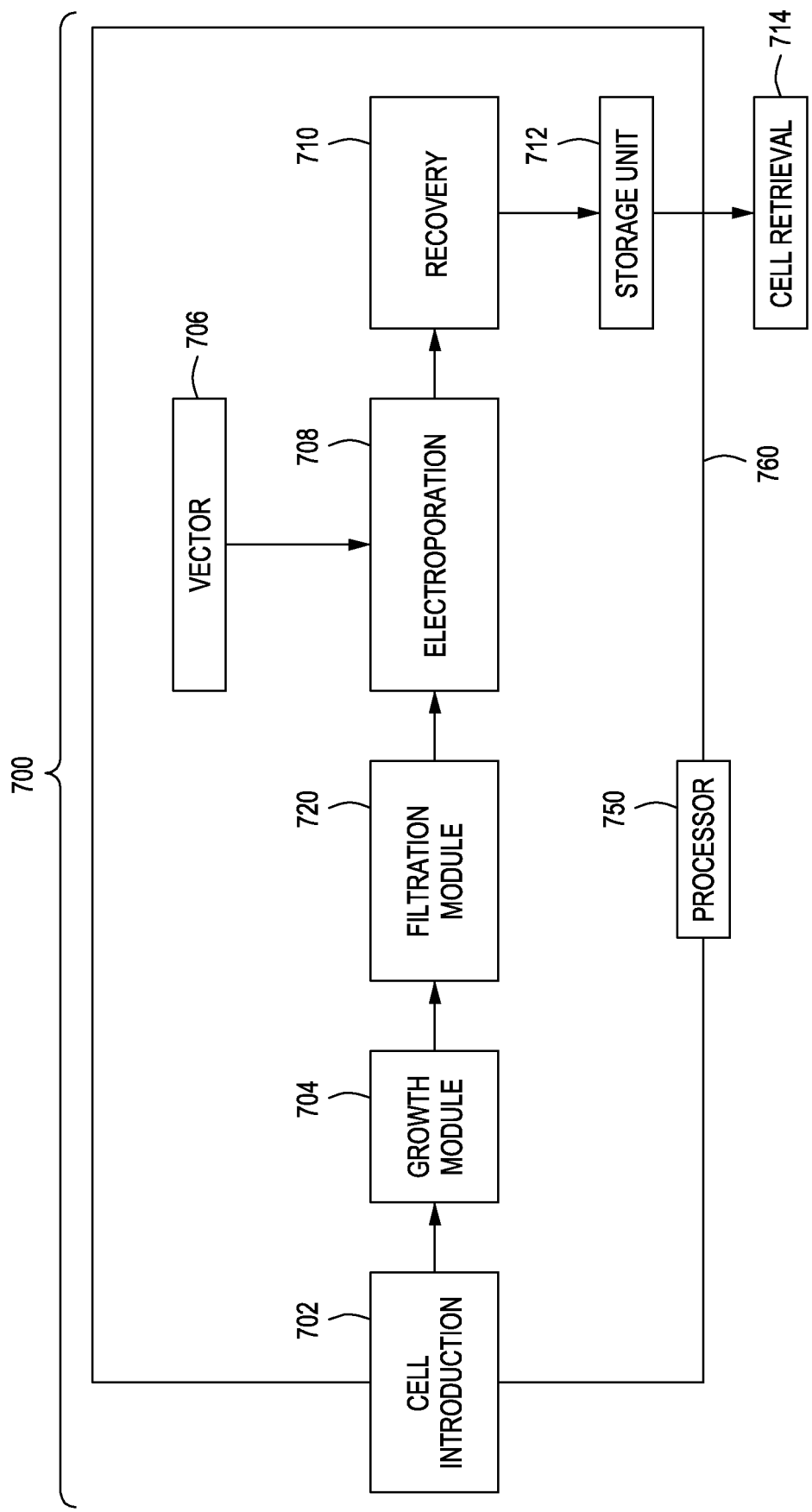
FIGS. 7A-7C are simplified block diagrams of exemplary automated multi-module cell processing systems in which the electroporation device may be used.

Use of the Compound Electroporator in Exemplary Automated Multi-Module Cell Processing Systems As described above, the electroporation devices and modules are used as components in an automated multi-module processing system. A general exemplary embodiment of a multi-module cell processing system is shown in FIG. 7A. In some embodiments, the cell processing system 700 may include a housing 760, a receptacle for introducing cells to be transformed or transfected 702, and a growth module 704. The cells to be transformed are transferred from a reservoir or receptacle to the growth module to be cultured until the cells hit a target OD. Once the cells hit the target OD, the growth module may cool or freeze the cells for later processing or the cells may be transferred to a filtration module 720 where the cells are rendered electrocompetent and concentrated. The filtration module 720 comprises e.g., a filter to treat the cells to make them electrocompetent and concentrate the electrocompetent cells. In one example, 20 ml of cells+growth media is concentrated to 400 µl cells in 10% glycerol. Once the electrocompetent cells have been concentrated, the cells are transferred to an electroporation device to be transformed with a desired nucleic acid. In addition to the receptacle for receiving cells, the multi-module cell processing system includes a receptacle for storing the nucleic acids to be electroporated into the cells 706. The nucleic acids are transferred to the electroporation module 708 (comprising, e.g., the electroporation device, liquid handling device, and electroporation station) which already contains the concentrated electrocompetent cells grown to the specified OD, where the nucleic acids are introduced into the cells. Following electroporation, the transformed cells are transferred into, e.g., a recovery module 710. Here, the cells are allowed to recover from the electroporation procedure.

In some embodiments, after recovery the cells are transferred to a storage module 712 to be stored at, e.g., 4° C. or frozen. The cells can then be retrieved from a retrieval module 714 and used for protein expression or further studies off-line. The automated multi-module cell processing system is controlled by a processor 750 configured to operate the instrument based on user input or one or more scripts. The processor 750 may control the timing, duration, temperature, and other operations (including, e.g., dispensing reagents) of the various modules of the system 700 as specified by one or more scripts. In addition to or as an alternative to the one or more scripts, the processor may be programmed with standard protocol parameters from which a user may select; alternatively, a user may select one or all parameters manually. The script may specify, e.g., the wavelength at which OD is read in the cell growth module, the target OD to which the cells are grown, the target time at which the cells will reach the target OD, and the time, voltage, and/or wave form for electroporation. The processor may notify the user (e.g., via an application to a smart phone or other device) that the cells have reached the target OD as well as update the user as to the progress of the cells in the cell growth module, electroporation device, filtration module, recovery module, etc. in the automated multi-module cell processing system.

Figure 7B:
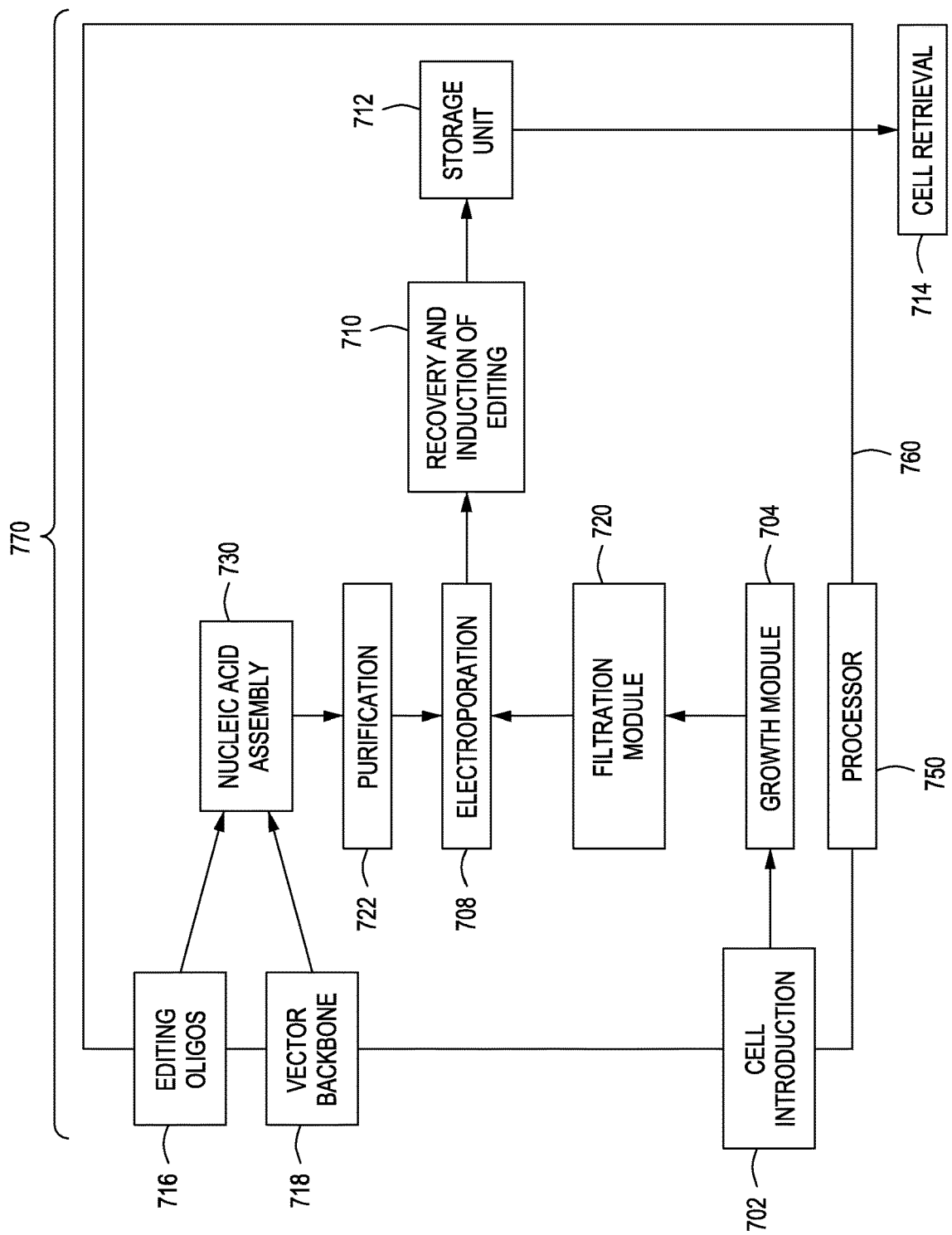

A second embodiment of an automated multi-module cell processing system is shown in FIG. 7B. As with the embodiment shown in FIG. 7A, the cell processing system 770 may include a housing 760, a reservoir of cells in, e.g., the reagent cartridge to be transformed or transfected 702, and a growth module (a cell growth device) 704. The cells to be transformed are transferred from a reservoir to the growth module to be cultured until the cells hit a target OD. Once the cells hit the target OD, the growth module may cool or freeze the cells for later processing, or the cells may be transferred to a filtration module 720 where the cells are rendered electrocompetent and concentrated to a volume optimal for cell transformation/electroporation as described above in relation to FIG. 7A. Once concentrated, the cells are then transferred to the electroporation module 708.

In addition to the reservoir for storing the cells, the reagent cartridge may include a reservoir for storing editing oligonucleotides 716 and a reservoir for storing an expression vector backbone 718. Both the editing oligonucleotides and the expression vector backbone are transferred from the reagent cartridge to a nucleic acid assembly module 720 (such as the nucleic acid assembly module described above), where the editing oligonucleotides are inserted into the expression vector backbone. The assembled nucleic acids may be transferred into an optional purification module 722 for desalting and/or other purification procedures needed to prepare the assembled nucleic acids for transformation. Once the processes carried out by the purification module 722 are complete, the assembled nucleic acids are transferred to the electroporation module 708, which already contains the cell culture grown to a target OD. In electroporation module 708 the nucleic acids are introduced into the cells. Following electroporation, the cells are transferred into a combined recovery and editing module 712. As described above, in some embodiments the automated multi-module cell processing system 700 is a system that performs gene editing such as an RNA-direct nuclease editing system. For example, see in U.S. Ser. No. 16/024,816, filed Jun. 30, 2018; U.S. Ser. No. 16/024,831, filed Jun. 30, 2018, U.S. Ser. No. 62/657,651, filed Apr. 13, 2018; and U.S. Ser. No. 62/657,654, filed May 14, 2018. In the recovery and editing module 710, the cells are allowed to recover post-transformation, and the cells express the editing oligonucleotides that edit desired genes in the cells as described below.

Following editing, the cells are transferred to a storage module 714, where the cells can be stored at, e.g., 4° C. until the cells are retrieved for further study. The multi-module cell processing system is controlled by a processor 750 configured to operate the instrument based on user input, as directed by one or more scripts, or as a combination of user input or a script. The processor 750 may control the timing, duration, temperature, and operations of the various modules of the system 770 and the dispensing of reagents, and the time, voltage and waveform for electroporation. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the automated multi-module system.

Certain embodiments of the multi-module processing system such as the system depicted in FIG. 7B include a nucleic acid assembly module (for example, a Gibson Assembly® module, a Gap Repair module as used in yeast, or a module that performs, the polymerase chain reaction, ligation chain reaction, ligase detection reaction, ligation, circular polymerase extension cloning, or other cloning methods) 730. The nucleic acid assembly module 730 is configured to assemble the nucleic acids necessary to facilitate genome editing events. In a nuclease-directed genome editing system, a vector comprises one or more regulatory elements operably linked to a polynucleotide sequence encoding a nucleic acid-guided nuclease. Thus, the nucleic acid assembly module 730 in these embodiments is configured to assemble the expression vector expressing a nucleic acid guided nuclease. The nucleic acid assembly module 730 may be temperature controlled depending upon the type of nucleic acid assembly used in the instrument. For example, when a Gibson Assembly® protocol is utilized, the module is configured to have the ability to reach and hold 50° C. If PCR is performed as part of the automated multi-module cell processing system, the nucleic acid assembly module is configured to thermocycle between temperatures. The temperatures and duration for maintaining temperatures can be effected by a preprogrammed set of parameters (as dictated by a script or programmed into the processor), or manually controlled by the user using the processor.

As described above, in one embodiment the automated multi-module cell processing system 770 is a nuclease-directed genome editing system. Multiple nuclease-based systems exist for providing edits into a cell, and each can be used in either single editing systems as could be performed in the automated system 700 of FIG. 7A; sequential editing systems as could be performed in the automated system 780 of FIG. 7C described below, e.g., using different nuclease-directed systems sequentially to provide two or more genome edits in a cell; and/or recursive editing systems as could be performed in the automated system 780 of FIG. 7C, e.g. utilizing a single nuclease-directed system to introduce two or more genome edits in a cell. Automated nuclease-directed processing systems use the nucleases to cleave the cell's genome, to introduce one or more edits into a target region of the cell's genome, or both. Nuclease-directed genome editing mechanisms include zinc-finger editing mechanisms (see Urnov et al., Nature Reviews Genetics, 11:636-64 (2010)), meganuclease editing mechanisms (see Epinat et al., Nucleic Acids Research, 31(11):2952-62 (2003); and Arnould et al., Journal of Molecular Biology, 371(1):49-65 (2007)), and RNA-guided editing mechanisms (see Jinek et al., Science, 337:816-21 (2012); and Mali et al, Science, 339:823-26 (2013)). In particular embodiments, the nuclease editing system is an inducible system that allows control of the timing of the editing (see Campbell, Biochem J., 473(17): 2573-2589 (2016); and Dow et al., Nature Biotechnology, 33390-94 (2015)). That is, when the cell or population of cells comprising a nucleic acid-guided nuclease encoding DNA is in the presence of the inducer molecule, expression of the nuclease can occur. The ability to modulate nuclease activity can reduce off-target cleavage and facilitate precise genome engineering.

Figure 7C:
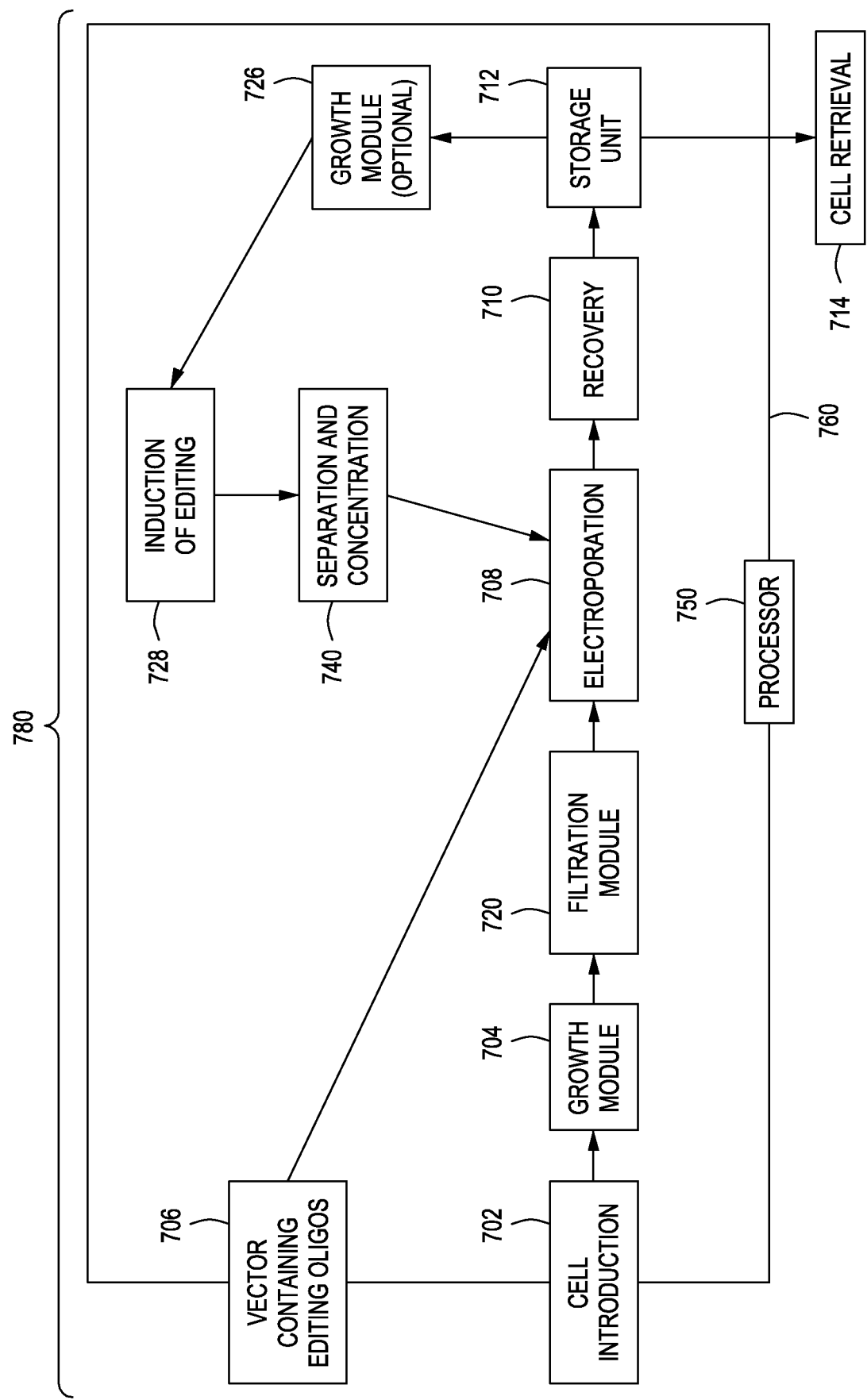

A third embodiment of a multi-module cell processing system is shown in FIG. 7C. This embodiment depicts an exemplary system 780 that performs recursive gene editing on a cell population. As with the embodiment shown in FIGS. 7A and 7B, the cell processing system 780 may include a housing 760, a reservoir in a reagent cartridge for storing cells to be transformed or transfected 702, and a cell growth module (a cell growth device) 704. The cells to be transformed are transferred from a reservoir to the cell growth module to be cultured until the cells hit a target OD.

Once the cells hit the target OD, the growth module may cool or freeze the cells for later processing, or the cells may be transferred to a filtration module 730 where the cells are rendered electrocompetent, and the volume of the cells may be reduced substantially. Once the cells have been concentrated to an appropriate volume, the cells are transferred to electroporation module 708. In addition to the reservoir for storing cells, the multi-module cell processing system includes a reservoir for storing the vector comprising editing oligonucleotides 706. The assembled nucleic acids are transferred to the electroporation module 708, which already contains the cell culture grown to a target OD. In the electroporation module 708, the nucleic acids are electroporated into the cells. Following electroporation, the cells are transferred into a recovery module 724. In the recovery module 724, the cells are allowed to recover post-transformation.

The cells are transferred to a storage module 712, where the cells can be stored at, e.g., 4° C. until the cells are retrieved for further study, or the cells are transferred to a second, optional, growth module 726. Once the cells hit a target OD, the second growth module may cool or freeze the cells for later processing, or transfer the cells to, e.g., an editing module 728 where an inducible nuclease is expressed in the cells, e.g., by introduction of heat or the introduction of an inducer molecule for expression of the nuclease. After editing, the cells are transferred to a separation and filtration module 730 where the cells are separated and/or concentrated from the editing solution in preparation for transfer to electroporation module 708.

In electroporation module 708, the cells are transformed by a second set of editing oligos (or other type of oligos) and the cycle is repeated until the cells have been transformed and edited by a desired number of, e.g., editing oligonucleotides. As discussed above in relation to FIGS. 7A and 7B, the multi-module cell processing system is controlled by a processor 750 configured to operate the instrument based on user input or is controlled by one or more scripts including at least one script associated with the reagent cartridge. The processor 750 may control the timing, duration, and temperature of various processes; the dispensing of reagents; the time, voltage and waveform for electroporation; and other operations of the various modules of the system 780. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing system.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶ 6.

We claim:

1. An automated multi-module cell processing system comprising:
    an electroporation module comprising an automated liquid handling device and a multi-unit electroporation module, wherein each electroporation module comprises
        a housing configured to engage with a pipette from the automated liquid handling device;
        an electroporation cuvette comprising an electroporation chamber defined by walls and wherein the electroporation cuvette is configured to receive a liquid from the automated liquid handling device; and
        a sipper in fluid communication with the electroporation chamber, wherein the sipper is configured for intake and output of a sample comprising cells to be electroporated in the electroporation cuvette; and
    a growth module;
    a recovery module; and
    a processor.

2. The automated multi-module cell processing system of claim 1, wherein the pipette is an automatic air displacement pipette.

3. The automated multi-module cell processing system of claim 1, wherein the pipette is a multi-channel pipette.

4. The automated multi-module cell processing system of claim 1, wherein the sample comprises bacterial cells.

5. The automated multi-module cell processing system of claim 1, wherein the sample comprises mammalian cells.

6. The automated multi-module cell processing system of claim 1, wherein the liquid comprises one or more materials to be electroporated into the cells selected from nucleic acids, peptides, proteins, hormones, cytokines, chemokines, drugs, or drug precursors.

7. The automated multi-module cell processing system of claim 6, wherein the liquid comprises nucleic acids.

8. The automated multi-module cell processing system of claim 1, wherein the liquid comprises at least one reagent of an RNA-directed nuclease editing system.

9. The automated multi-module cell processing system of claim 1, wherein the processor is configured to read an optical density (OD) of the cells in the growth module.

10. The automated multi-module cell processing system of claim 9, wherein the processor is configured to instruct the growth module that the cells have reached the target OD.

11. The automated multi-module cell processing system of claim 1, wherein the processor is configured to provide input for the pipette to move the cells into the recovery module after electroporation.

12. The automated multi-module cell processing system of claim 1, wherein the processor is configured to provide input for each electroporation module for dispensing of reagents via the automated liquid handling device.

13. The automated multi-module cell processing system of claim 1, wherein the processor is configured to provide input for each electroporation module for the time, voltage or waveform for electroporation.

14. The automated multi-module cell processing system of claim 1, further comprising a storage module.

15. The automated multi-module cell processing system of claim 14, wherein the storage module stores the cells at 4° C. or lower temperatures.

16. A method for electroporating a cell sample using the automated multi-module cell processing system of claim 1, comprising the steps of;
    moving the electroporation cuvette to a position to receive the liquid from the automated liquid handling device;
    electroporating the sample comprising cells in the electroporation chamber of the electroporation cuvette;
    moving the electroporation device to a position to dispense the electroporated cell sample into the recovery module; and
    dispensing the cell sample from the electroporation chambers through the sippers and into the recovery module.

17. The method claim 16, wherein the recovery module comprises recovery medium to allow the pores of the cells to close and the cell membrane to recover from the electroporation process.

18. A method for electroporating a cell sample using the automated multi-module cell processing system of claim 1, comprising the steps of;
    dispensing a sample from the growth module into the electroporation cuvette through the sippers;
    moving the electroporation cuvette to a position to receive the liquid from the automated liquid handling device;
    electroporating the sample comprising cells in the electroporation chamber of the electroporation cuvette;
    moving the electroporation device to a position to dispense the electroporated cell sample into the recovery module; and
    dispensing the cell sample from the electroporation chambers through the sippers and into the recovery module.

* * * * *